United States Patent [19]

DeLong

[11] 4,210,647

[45] Jul. 1, 1980

[54] ANTIVIRAL COMBINATIONS

[75] Inventor: Donald C. DeLong, Indianapolis, Ind.

[73] Assignee: Eli Lilly and Company, Indianapolis, Ind.

[21] Appl. No.: 49,671

[22] Filed: Jun. 18, 1979

[51] Int. Cl.$^2$ .................... A61K 31/495; A61K 31/13
[52] U.S. Cl. .................................... 424/250; 424/325
[58] Field of Search ................................ 424/250, 325

[56] References Cited

FOREIGN PATENT DOCUMENTS 1408675 10/1975 United Kingdom .

Primary Examiner—Jerome D. Goldberg
Attorney, Agent, or Firm—James L. Rowe; Arthur R. Whale

[57] ABSTRACT

Antiviral combinations containing a 2-ester-substituted-3,4-dihydro-3-oxoquinoxaline and a hindered amine.

1 Claim, No Drawings

ANTIVIRAL COMBINATIONS

BACKGROUND OF THE INVENTION

2-Ester-substituted-3,4-dihydro-3-oxoquinoxalines are described as antiviral agents in copending application Ser. No. 953,157, filed Oct. 20, 1978. The compounds are particularly useful in that they show antiviral activity against both A and B strains of influenza virus. The antiviral activity of 1-aminoadamantane (amantidine, adamantylamine) was first disclosed by Davies et al. *Science*, 144, 862 (1964). 1-aminoadamantane is said to be active against influenza virus $A^2$ strain prophylactically. The compound also may have some use in the prophylaxis of Asian flu strains antigenically related to strain $A^2$. 3-Methyl-1-aminoadamantane, dl-cyclooctylamine, 2-norbornylamine and 1-adamantyl-1-aminoethane (rimantadine) have all been shown to be antiviral agents, both by myself and those working with me and by those working in other laboratories.

SUMMARY OF THE INVENTION

This invention provides a combination of a 2-ester-substituted-3,4-dihydro-3-oxoquinoxaline of the formula

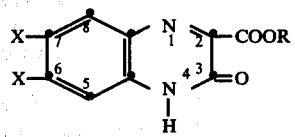

I wherein each X is separately Cl or Br and R is methyl or ethyl plus a hindered amine selected from the group consisting of 1-aminoadamantane, (formula II below when $R^1$ is $NH_2$ and $R^2$ is H) 3-methyl-1-aminoadamantane (formula II below wherein $R^1$ is $NH_2$ and $R^2$ is methyl), 1-adamantyl-1-aminoethane (formula II below wherein $R^1$ is

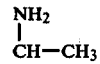

and $R^2$ is $CH_3$ or H), dl-cyclooctylamine and nobornanamine also referred to as 1-aminonorbornane and 2-aminobicyclo[2.2.1]heptane (formula III below).

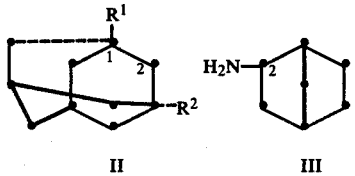

II   III

The above combination of antiviral drugs can be administered both prophylactically and therapeutically; i.e., both pre and post-infection. The combination can thus be given to mammals exposed to influenza virus to abort the viral infection as well as to mammals who have contracted an influenzal infection and are in need of a viral growth suppressing agent. Whether given before or after viral infection is present, the above combination will suppress the growth of both A and B strains of influenza virus. It is a particular advantage of my novel antiviral drug combination that a determination of the strain of influenza virus causing a particular infection need not be made since the combination is effective against both A and B strains.

The customary dose levels used in my novel antiviral combination vary widely depending on weight, size, body surface etc. of the particular mammalian species involved. With mice, for example, a single dose will contain from 20 to 160 mg./kg. of a quinoxaline according to formula I above plus from 10–80 mg./kg. of 1-aminoadamantane or from 5–50 mg./kg. of 3-methyl-1-aminoadamantane or 10–80 mg./kg. each of dl-cyclooctylamine, 2-aminonorbornane, or 1-(1-adamantyl)-1-aminoethane. For humans, the dose level is from 1/10 to 1/50 that of the dosage for mice, i.e., from 0.5–5 mg./kg. of a quinoxaline according to formula I plus 0.3–3 mg./kg. of 1-aminoadamantane or about 0.2–2 mg./kg. of 3-methylaminoadamantane or 0.3–3 mg./kg. of dicyclooctylamine, 2-aminonorbornane or 1-(1-adamantyl)-1-aminoethane. An average daily dosage schedule for humans would be from 30–300 mg. of a quinoxaline plus 15–200 mg. of 1-aminoadamantane twice a day. Dosage schedules for other combinations can be derived from the above data, coupled with a knowledge of dosage variation according to mammalian species with other drugs. The dosage form containing a quinoxaline of formula I plus a hindered amine containing drug-weights coming within the above ranges, is usually administered for four days consecutively although dosages of 1, 2 or 3 day duration will also provide good results as regards the viral infection.

Quinoxalines according to formula I above are prepared by reacting a 4,5-dihalophenylenediamine with a dialkyl mesoxalate according to the following reaction scheme Reaction Scheme 1

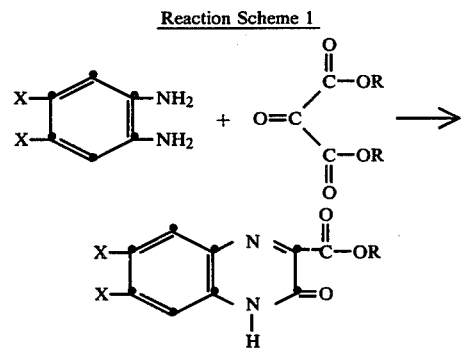

wherein R and X have the previously assigned significance. The following examples illustrate the procedure of Reaction Scheme I for preparing compound according to formula I above.

EXAMPLE 1

Preparation of Ethyl 6,7-Dichloro-3,4-dihydro-3-oxo-2-quinoxaline Carboxylate

A solution of 17.7 g. of 4,5-dichloro-o-phenylenediamine in 200 ml. of anhydrous ethanol was prepared. A 17.4 g. batch of diethyl 2-ketomalonate were added to this solution and the mixture was heated to refluxing temperature for about 17 hours. The volatile constituents were removed by evaporation in vacuo. Recrystallization of the residue from ethanol yielded 20 g. of ethyl 6,7-dichloro-3,4-dihydro-3-oxo-2-quinoxaline carboxylate formed in the above reaction, melting in the range 226°–227° C.

EXAMPLE 2

Preparation of Ethyl 6,7-dibromo-2,3-dihydro-3-oxoquinoxaline Carboxylate

Ten g. of 3,4-dibromoaniline were mixed with 40 ml. of acetic anhydride. The resulting reaction mixture was heated to a temperature in the range 100°–105° C. for one hour after which time it was poured over a mixture of ice and water. After stirring overnight, the aqueous mixture yielded an off-white precipitate weighing 11.5 g. and melting at 90°–95° C. comprising 3,4-dibromoacetanilide.

2.5 g. of 3,4-dibromoacetanilide were mixed with 8 ml. of 18 N aqueous sulfuric acid at 0° C. 1.5 g. of propyl nitrate were added while maintaining the reaction temperature in the range 0°–2° C. The chilled reaction mixture was stirred for one hour at the same temperature and then poured over an ice-water mixture. A yellow solid comprising 3,4-dibromo-6-nitroacetanilide formed in the above reaction precipitated and was collected by filtration. Recrystallization from ethanol yielded 1.2 g. of 3,4-dibromo-6-nitroacetanilide melting at 140°–141° C. after recrystallization from ethanol.

One gram of 3,4-dibromo-6-nitroacetanilide was heated to refluxing temperature for 30 minutes with 30 ml. of 6 N aqueous hydrochloric acid. The reaction mixture was then poured over an ice-water mixture with stirring. The pH of the solution was adjusted to 12 with alkali. The resulting bright yellow precipitate was separated by filtration, washed and dried; yield=0.85 g of 3,4-dibromo-6-nitroaniline melting at 204°–205° C.

Five grams of 3,4-dibromo-6-nitroaniline were suspended in 200 ml. of anhydrous ethanol to which was added about 10 g. of Raney nickel. The hydrogenation mixture was placed in a low pressure hydrogenation apparatus at a hydrogen pressure of 55 psi. A rapid uptake of hydrogen occurred which ceased after about 25 minutes, at which time the deep yellow color originally present had been discharged indicating complete reduction of the nitro group to an amino group. The hydrogenation was continued for another half hour and the hydrogenation mixture was then worked up by filtering off the catalyst, washing the filtered catalyst, and stripping the volatile constituents from the filtrate. A yield of 4.1 g. of 4,5-dibromo-o-phenylenediamine was obtained.

4,5-Dibromo-o-phenylaminediamine was cyclized to the corresponding quinoxaline carboxylic acid ester by the procedure of Example 1 utilizing 4.1 g. of the diamine and 2.7 g. of diethyl ketomalonate in 75 ml. of anhydrous ethanol. Ethyl 6,7-dibromo-3,4-dihydro-3-oxo-2-quinoxaline carboxylate thus prepared melted at 235°–236° C. (yield=3.9 g.).

EXAMPLE 3

Preparation of Ethyl 6(7)-Chloro-7(6)-bromo-3,4-dihydro-3-oxo-2-quinoxaline Carboxylate 3-Chloro-4-bromoacetanilide prepared by the procedure of Example 2 was nitrated in 18 M aqueous sulfuric acid with propyl nitrate at 0° C. according to the procedure of Example 2. The product of the reaction was worked up by adding it to a mixture of ice and water with stirring. A yellow powder comprising 3-chloro-4-bromo-6-nitroacetanilide precipitated and was collected by filtration. Recrystallization from ethanol gave crystals melting at 128°–130° C.; yield=38 g.

3-Chloro-4-bromo-6-nitroacetanilide was hydrolyzed to the free amine by the process of Example 2. Reduction of 5 g. of 3-chloro-4-bromo-6-nitroaniline thus formed with Raney nickel by the procedure of Example 2 yielded 3.35 g. of 4(5)-chloro-5(4)-bromo-o-phenylenediamine. A 1.66 g. portion of the diamine were reacted with 0.85 g. of diethyl ketomalonate by refluxing in a mutual solvent for 2.5 hours. Yellow, needle-like crystals comprising ethyl 6(7)-chloro-7(6)-bromo-3,4-dihydro-3-oxo-2-quinoxaline carboxylate precipitated and were collected by filtration; mp=185°–195° C.; yield=111 g.

In the above reaction scheme, when each X represents a different group, the product of the reaction of the substituted o-phenylenediamine and diethyl mesoxalate produces a mixture of compounds as seen in Example 3. A reaction procedure for the unequivocal synthesis of a compound coming within the scope of this invention in which the X's are different is set forth in Reaction Scheme 2 below:

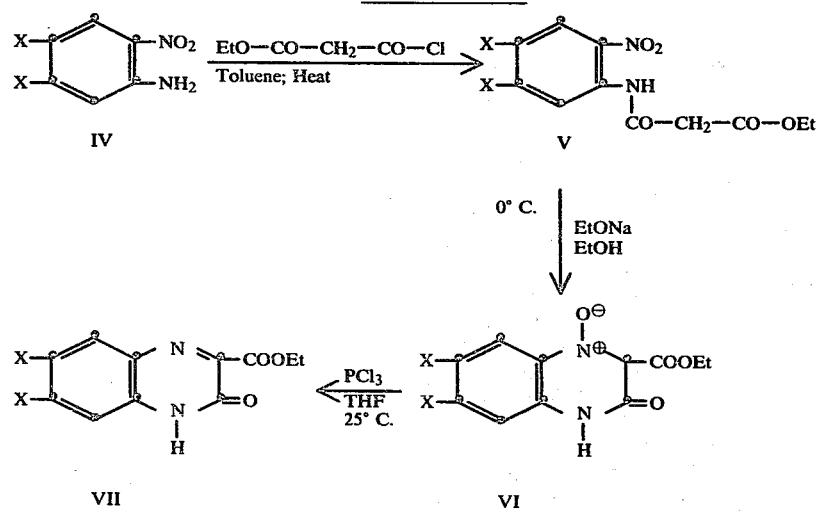

Reaction Scheme 2 in which one X is Br and the other Cl.

According to Reaction Scheme 2, a 6-nitro-3,4-dihaloaniline (IV) is reacted with ethyl malonyl chloride (or other alkyl malonyl halide) to give the corresponding ethyl malonyl amide derivative on the aniline nitrogen (V). A base catalyzed annelation using sodium ethoxide at 0° C. yields the quinoxaline $N^1$-oxide (VI), treatment of which with phosphorus trichloride in tetrahydrofuran (THF) at ambient temperature produces unambiguously a 6,7-substituted-3,4-dihydro-3-oxo-2-quinoxaline carboxylate, ethyl ester (VII). This procedure is illustrated in Example 4 below.

EXAMPLE 4

Preparation of Ethyl 6-Chloro-7-bromo-3,4-dihydro-3-oxo-2-quinoxaline Carboxylate Five grams of 3-chloro-4-bromo-6-nitroaniline were dissolved in 150 ml. of benzene. Five grams of the acid chloride of monoethyl malonate were added with stirring under a nitrogen atmosphere. The reaction mixture was heated to refluxing temperature overnight. Thin-layer chromatography indicated that the reaction was essentially complete at this time. The reaction mixture was cooled and the benzene removed by evaporation in vacuo. The residue containing N-ethoxycarbonylacetyl 3-chloro-4-bromo-6-nitroaniline formed in the above reaction, was recrystallized from anhydrous ethanol to yield fluffy yellow crystals melting at 119°–121° C.

Sodium ethylate was prepared under anhydrous conditions from 35 ml. of anhydrous ethanol and 1 g. of sodium in a nitrogen atmosphere. The mixture was stirred until the sodium was dissolved completely after which time the mixture was chilled to about 0° C. N-ethoxycarbonylacetyl 3-chloro-4-bromo-6-nitroaniline was added and the resulting mixture was stirred at 0° C. for about 3 hours. The reaction was then quenched by adding it to 300 ml. of 1 N aqueous hydrochloric acid at 0° C. This aqueous mixture was stirred until a solid precipitate formed. The precipitate was separated by filtration, dried, and the filter cake was recrystallized from anhydrous ethanol. Ethyl 6-chloro-7-bromo-3-oxo-2-quinoxaline carboxylate N-oxide thus prepared melted at 219°–221° C.; yield=2 g.

Analysis Calc.: C, 38.01; H, 2.32; N, 8.06. Found: C, 37.79; H, 2.35; N, 8.24.

One gram of ethyl 6-chloro-7-bromo-3,4-dihydro-3-oxo-2-quinoxaline carboxylate N-oxide was dissolved in 50 ml. of THF. Six ml. of phosphorus trichloride were added and the resulting mixture heated gently at refluxing temperature overnight. The reaction mixture was poured into 500 ml. of an ice-water mixture. A solid, comprising ethyl 6-chloro-7-bromo-3,4-dihydro-3-oxo-2-quinoxaline carboxylate formed in the above reaction, was separated by filtration; melting point=203°–205° C.; yield=0.6 g.

While it is easier to have an ethyl or methyl ester in the final product (I) by starting with the desired diethyl or dimethyl mesoxalate, it is possible to hydrolyze the ester produced and reesterify the resulting acid with the other alcohol as illustrated below.

EXAMPLE 5

Hydrolysis of Ethyl 6,7-Dichloro-3,4-dihydro-2-oxo-3-quinoxaline Carboxylate

One gram of ethyl 6,7-dichloro-3,4-dihydro-2-oxo-3-quinoxaline carboxylate was dissolved in a mixture of 25 ml. of isopropanol and 75 ml. of water. Five grams of potassium hydroxide were added and the resulting mixture heated to reflux temperature for 5 minutes. The hot reaction mixture was decolorized with activated charcoal and filtered. The filtrate was acidified with 12 N aqueous hydrochloric acid. Needle-like yellow crystals precipitated comprising 6,7-dichloro-2-oxo-3-quinoxaline carboxylic acid formed in the above hydrolysis. The acid was collected by filtration.

EXAMPLE 6

Preparation of Esters 6,7-Dichloro-3,4-dihydro-3-oxo-2-quinoxaline carboxylic acid prepared from the corresponding ethyl ester by the procedure of Example 5 was esterified with methanol according to the following procedure: Two grams of the free acid and 20 ml. of anhydrous methanol were mixed with a catalytic quantity of boron trifluoride etherate dissolved in methanol. The mixture was heated to refluxing temperature for 60 hours after which time it was cooled and filtered. Methyl 6,7-dichloro-3,4-dihydro-3-oxo-2-quinoxaline carboxylate separated and was isolated by filtration; weight=153 g.; color=greenish yellow; mp=258°–260° C.

The hindered amine component of my novel antiviral combination can be prepared by methods available in the art.

The synergistic antiviral effects of the combination of a quinoxaline and a hindered amine is illustrated by the following experiments. Each component, the quinoxaline and the hindered amine, were tested individually at a series of dose levels against Ann Arbor or Maryland B strains of influenza virus. Combinations of the two drugs using a dose level corresponding to one already used in determining the efficacy of the individual components was employed. The general procedure is that set forth in Redman et al., *Antimicrobial Agents and Chemotherapy*, 497 (1966). The mean day of death for the treated and untreated mice was recorded and the number of survivors out of the total number of mice at each dose level also recorded. In addition a survival index was computed. The survival index is a composite measure of effectiveness incorporating both time of death, the number of survivors into a single variable in accordance with the above paper by Redman et al. In tables 1 and 2 which follow, the drugs were given by the intraperitoneal route. The dosage was administered 24 hours and 4 hours prior to inoculation with the virus and 24 and 48 hours after inoculation. Groups of 18 mice were used at each dose level and there was a control group which was given only the pharmaceutical extending medium for each determination. White swiss (McAllister strain) females weighing 11 to 13 grams were used. Statistically-significant data is indicated in the tables in each instance by an asterisk. For ease of following the data in the tables, each compound employed in the experiment has been given a letter according to the following chart A. ethyl 6,7-dibromo-3,4,-dihydro-3-oxoquinoxaline-2-carboxylate,
B. ethyl-6,7-dichloro-3,4-dihydro-3-oxoquinoxaline-2-carboxylate,
M. 1-aminoadamantane hydrochloride,
N. 3-methyl-1-adamantane hydrochloride,
O. dl-cyclooctylamine,
P. 1(1-adamantyl)-1-amino ethane, and R. 2-aminonorbornane.

In each table that follows the strain of virus is indicated at the head of the table. Column one gives the letter assigned to a given compound, column 2 the dose in mg./kg., column 3, the survival index at that dose level, column 4, the median day of death, column 5, the number of survivors and column 6 the number of animals. Table 3 gives similar information for the administration of combinations of adamantylamine hydrochloride and ethyl 6,7-dibromo-3,4-dihydro-3-oxoquinoxaline carboxylate administered to mice by the oral route at a series of dose levels at the same time intervals before and after inoculation of the mice with the Ann Arbor strain of influenza virus as for Tables 1 and 2.

Table 1

Ann Arbor Strain - I.P.

| Compound | Dose in mg/kg | Survival Index | Medium Day of Death | Number Survivors Number Animals |
|---|---|---|---|---|
| M | 40 | 5.26* | 9.1 | 10/17 |
| M | 80 | 5.67* | 8.8 | 14/17 |
| A | 40 | 2.79 | 7.9 | 4/18 |
| A | 80 | 3.62 | 8.6 | 4/18 |
| M+A | 40+40 | 6.17* | 8.0 | 17/18 |
| Control | 0 | 2.93 | 8.1 | 7/35 |
| M | 40 | 6.20* | 9.0 | 7/17 |
| A | 80 | 5.74* | 8.9 | 3/18 |
| M+A | 20+40 | 6.70 | 9.1 | 11/18 |
| M+A | 10+20 | 5.14* | 8.5 | 5/18 |
| M+A | 5+10 | 4.73* | 8.2 | 5/18 |
| Control | 0 | 2.46 | 7.5 | 1/36 |
| M | 40 | 7.23* | 9.7 | 7/18 |
| M | 80 | 6.52* | 9.2 | 9/18 |
| A | 40 | 4.82* | 8.9 | 1/18 |
| A | 80 | 6.25* | 9.4 | 4/18 |
| M+A | 40+40 | 6.78* | 9.0 | 13/18 |
| M+A | 20+20 | 7.04* | 9.5 | 7/18 |
| M+A | 10+10 | 6.27* | 9.3 | 5/18 |
| Control | 0 | 2.21 | 8.1 | 2/36 |
| M | 80 | 6.02* | 8.9 | 8/17 |
| M+A | 10+20 | 6.86* | 8.5 | 14/18 |
| M+A | 20+60 | 7.45* | 9.7 | 12/18 |
| M+A | 30+60 | 7.38* | 9.3 | 14/18 |
| Control | 0 | 2.60 | 8.1 | 1/36 |
| N | 25 | 4.07* | 7.9 | 4/18 |
| N | 50 | 5.53* | 9.1 | 5/18 |
| A | 40 | 4.86* | 8.7 | 2/18 |
| A | 80 | 5.51* | 9.3 | 3/18 |
| N+A | 25+40 | 5.97* | 9.0 | 8/18 |
| Control | 0 | 2.39 | 7.6 | 0/36 |
| N | 20 | 2.89 | 7.9 | 1/18 |
| N | 40 | 3.69 | 8.2 | 1/18 |
| A | 40 | 3.94* | 8.2 | 1/18 |
| A | 80 | 4.78* | 8.7 | 0/18 |
| N+A | 20+40 | 6.13* | 8.8 | 9/18 |
| Control | 0 | 2.36 | 7.6 | 2/36 |
| O | 40 | 4.05* | 8.4 | 1/18 |
| O | 80 | 4.05* | 8.3 | 2/18 |
| A | 40 | 3.36 | 8.0 | 2/18 |
| A | 80 | 4.06* | 8.4 | 1/18 |
| O+A | 40+40 | 5.90* | 8.8 | 6/18 |
| Control | 0 | 2.51 | 7.6 | 1/36 |
| M | 40 | 5.40* | 9.1 | 6/18 |
| M | 80 | 5.69* | 9.1 | 6/18 |
| B | 40 | 3.27 | 8.3 | 3/18 |
| B | 80 | 3.07 | 8.3 | 3/18 |
| M+B | 40+40 | 5.85* | 7.8 | 13/18 |
| Control | 0 | 1.71 | 7.7 | 4/36 |
| M | 40 | 3.85 | 8.7 | 2/18 |
| M | 80 | 4.42* | 8.7 | 6/17 |
| B | 40 | 2.87 | 8.3 | 1/17 |
| B | 80 | 3.24 | 8.5 | 1/18 |
| M+B | 40+40 | 5.68* | 9.4 | 9/18 |
| Control | 0 | 1.76 | 7.7 | 0/36 |
| O | 40 | 5.09* | 8.8 | 2/18 |
| O | 80 | 5.89* | 8.9 | 3/18 |
| A | 40 | 4.12* | 8.1 | 1/18 |
| A | 80 | 4.97* | 8.4 | 1/18 |
| O+A | 40+40 | 6.07* | 9.0 | 4/18 |

Table 1-continued

Ann Arbor Strain - I.P.

| Compound | Dose in mg/kg | Survival Index | Medium Day of Death | Number Survivors Number Animals |
|---|---|---|---|---|
| Control | 0 | 2.38 | 7.3 | 0/36 |
| P | 40 | 2.46 | 7.4 | 0/18 |
| P | 80 | 2.61 | 7.5 | 0/18 |
| A | 40 | 4.65* | 8.3 | 0/18 |
| A | 80 | 4.51* | 8.2 | 1/18 |
| P+A | 40+40 | 4.18* | 7.6 | 5/18 |
| Control | 0 | 2.31 | 7.3 | 1/36 |
| R | 40 | 5.91* | 9.5 | 7/18 |
| R | 80 | 7.20* | 10.0 | 14/18 |
| A | 40 | 2.86 | 7.9 | 4/18 |
| A | 80 | 3.98 | 8.9 | 3/18 |
| R+A | 40+40 | 7.30* | 10.0 | 16/18 |
| Control | 0 | 1.83 | 7.6 | 1/36 |
| O | 80 | 5.19* | 7.6 | 7/17 |
| A | 40 | 4.41 | 8.7 | 2/17 |
| A | 80 | 4.95 | 8.8 | 4/18 |
| O+A | 40+40 | 5.54* | 7.9 | 7/17 |
| Control | 0 | 2.75 | 8.1 | 1/36 |
| P | 40 | 2.36 | 8.0 | 1/18 |
| P | 80 | 3.21 | 7.8 | 1/18 |
| A | 40 | 5.99* | 8.9 | 1/18 |
| A | 80 | 6.26* | 8.9 | 3/18 |
| P+A | 40+40 | 4.27* | 8.2 | 2/18 |
| Control | 0 | 2.24 | 7.6 | 0/36 |

Table 2

Maryland B Strain - I.P.

| Compound | Dose in mg/kg | Survival Index | Medium Day of Death | Number Survivors Number Animals |
|---|---|---|---|---|
| M | 40 | 2.39 | 8.2 | 0/18 |
| A | 80 | 4.44* | 8.7 | 4/18 |
| M+A | 10+20 | 2.41 | 8.3 | 0/18 |
| M+A | 20+40 | 4.56* | 8.5 | 5/18 |
| M+A | 40+80 | 4.79* | 8.8 | 3/17 |
| Control |  | 2.20 | 8.2 | 1/36 |

Table 3

Ann Arbor Strain - Oral

| Compound | Dose in mg/kg | Survival Index | Medium Day of Death | Number Survivors Number Animals |
|---|---|---|---|---|
| M | 80 | 4.97* | 8.9 | 5/18 |
| M+A | 10+20 | 3.06* | 8.3 | 2/18 |
| M+A | 20+40 | 5.12 | 8.5 | 7/18 |
| M+A | 30+60 | 6.03* | 8.9 | 9/18 |
| M+A | 40+80 | 6.01* | 8.9 | 9/17 |
| Control | 0 | 2.83 | 8.4 | 2/35 |

The experimental results set forth in Tables 1-3 above, showing a synergistic effect between a quinoxaline of formula I and a hindered amine, involve protocols whereby the combination of drugs is administered either by the intraperitoneal route or orally. I prefer that the drugs be administered orally. For oral administration, a most advantageous mode of administration is by the use of gelatin capsules. For this purpose, a quantity of a quinoxaline ester according to formula I above and a quantity of a hindered amine preferably as an acid addition salt with a strong acid such as hydrochloric acid are mixed and the mixture diluted with a pharmaceutically acceptable extending medium such as starch. After thoroughly mixing, the mixture is loaded into empty gelatin capsules such that each capsule contains from 50 to 100 mg. of the acid addition salt of the hindered tertiary amine and from 50 to 100 mg. of the quinoxaline. Since it is known that the esters are slowly hydrolyzed in the presence of amine hydrochlorides and atmospheric moisture, one of the two ingredients, either the quinoxaline or the amine hydrochloride, should be coacervated with, for example, ethyl cellulose, shellac or an enteric coating composed of for example polyvinylacetatephthalate or hydroxypropylmethylcellulose phthalate. The teaching of U.S. Pat. No. 4,044,125 for inhibiting the hydrolysis of the ester, acetylsalicylic acid in the presence of a hydrochloride salt, d-propoxyphene hydrochloride, can be followed in which the composition is stabilized by the addition of the hydrochloride salt of an amino acid.

The novel drug combinations of this invention have the following desirable properties: The combination is more active in combating viral infections and suppressing viral growth in mammals in vivo than is either ingredient by itself, as evidenced by the side-by-side tests set forth in the above tables. There is not only a higher degree of protection but also a higher therapeutic ratio at the low drug levels than for each of the drugs by itself. There are also fewer side effects with the combination since the drugs act synergistically only in their effect against influenza virus and not in producing side effects. The synergistic combination is active against both A and B strains of influenza virus as exemplified by the Ann Arbor and Maryland "B" strains included in the above experimental work. Thirdly the combination has a low toxicity. Lastly and most importantly, the combination is active upon oral administration.

I claim:

1. A method of suppressing influenza virus infections in mammals which comprises administering to a mammal exposed to influenza virus a virus-suppressing amount of a combination containing from 0.5–5 mg/kg of ethyl 6,7-dibromo3-4-dihydro-3-oxquinoxaline carboylate and from 0.3–3 mg/kg of 1 aminoadamantane.

* * * * *